(12) United States Patent
Mikhail

(10) Patent No.: US 10,842,839 B2
(45) Date of Patent: *Nov. 24, 2020

(54) NATURAL FORMULATION FOR TREATING HANGOVER

(71) Applicant: RVRS, LLC, Newport Beach, CA (US)

(72) Inventor: Nader George Mikhail, Newport Beach, CA (US)

(73) Assignee: RVRS, LLC, Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/413,523

(22) Filed: May 15, 2019

(65) Prior Publication Data

US 2019/0262414 A1 Aug. 29, 2019

Related U.S. Application Data

(63) Continuation of application No. 15/345,143, filed on Nov. 7, 2016, now Pat. No. 10,357,529.

(51) Int. Cl.
| | |
|---|---|
| *A61K 36/82* | (2006.01) |
| *A61K 33/00* | (2006.01) |
| *A61K 36/28* | (2006.01) |
| *A61K 36/9068* | (2006.01) |
| *A61K 36/33* | (2006.01) |
| *A61K 36/72* | (2006.01) |
| *A61K 33/06* | (2006.01) |
| *A61K 33/30* | (2006.01) |
| *A61K 31/51* | (2006.01) |
| *A61K 31/525* | (2006.01) |
| *A61K 31/675* | (2006.01) |
| *A61K 31/714* | (2006.01) |
| *A61K 31/4415* | (2006.01) |
| *A61K 31/197* | (2006.01) |
| *A61K 31/4188* | (2006.01) |
| *A61K 31/519* | (2006.01) |
| *A61K 31/198* | (2006.01) |
| *A61K 45/06* | (2006.01) |
| *A61K 31/164* | (2006.01) |
| *A61K 31/455* | (2006.01) |
| *A61K 31/718* | (2006.01) |
| *A61K 33/08* | (2006.01) |
| *A61K 33/44* | (2006.01) |
| *A61K 38/06* | (2006.01) |
| *A61K 9/00* | (2006.01) |
| *A61K 31/375* | (2006.01) |
| *A61K 31/01* | (2006.01) |
| *A61K 31/355* | (2006.01) |
| *A61K 31/122* | (2006.01) |
| *A61K 31/047* | (2006.01) |
| *A61K 31/14* | (2006.01) |
| *A61K 31/07* | (2006.01) |

(52) U.S. Cl.
CPC ............ *A61K 36/82* (2013.01); *A61K 9/0095* (2013.01); *A61K 31/01* (2013.01); *A61K 31/047* (2013.01); *A61K 31/07* (2013.01); *A61K 31/122* (2013.01); *A61K 31/14* (2013.01); *A61K 31/164* (2013.01); *A61K 31/197* (2013.01); *A61K 31/198* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/675* (2013.01); *A61K 31/714* (2013.01); *A61K 31/718* (2013.01); *A61K 33/00* (2013.01); *A61K 33/06* (2013.01); *A61K 33/08* (2013.01); *A61K 33/30* (2013.01); *A61K 33/44* (2013.01); *A61K 36/28* (2013.01); *A61K 36/33* (2013.01); *A61K 36/72* (2013.01); *A61K 36/9068* (2013.01); *A61K 38/063* (2013.01); *A61K 45/06* (2013.01)

(58) Field of Classification Search
CPC ........ A61K 36/82; A61K 36/72; A61K 36/33; A61K 36/9068; A61K 38/063; A61K 31/519; A61K 31/4188; A61K 31/197; A61K 31/4415; A61K 31/714; A61K 31/675; A61K 31/525; A61K 31/51; A61K 31/718; A61K 31/455; A61K 31/164; A61K 31/198; A61K 33/30; A61K 33/06; A61K 33/00; A61K 33/44; A61K 33/08; A61K 9/0095; A61K 45/06
See application file for complete search history.

(56) References Cited

U.S. PATENT DOCUMENTS

| | | | | |
|---|---|---|---|---|
| 9,603,830 | B2* | 3/2017 | Powell | A61K 31/353 |
| 10,357,529 | B2* | 7/2019 | Mikhail | A61K 31/14 |
| 2001/0043956 | A1* | 11/2001 | Mirza | A61K 9/2013 |
| | | | | 424/725.1 |
| 2003/0219432 | A1* | 11/2003 | Crippen | A61K 31/551 |
| | | | | 424/125 |
| 2012/0164253 | A1* | 6/2012 | Ra | A61K 36/185 |
| | | | | 424/769 |
| 2014/0256760 | A1* | 9/2014 | Tolleth | A61K 31/385 |
| | | | | 514/276 |
| 2014/0314887 | A1* | 10/2014 | Paek | A61K 36/72 |
| | | | | 424/765 |
| 2015/0004282 | A1* | 1/2015 | Mills | A23L 23/00 |
| | | | | 426/72 |

OTHER PUBLICATIONS

Eng Abstract of KR 2007077946 A, Jul. 2007.*

(Continued)

*Primary Examiner* — Blessing M Fubara
(74) *Attorney, Agent, or Firm* — Knobbe, Martens, Olson & Bear, LLP

(57) ABSTRACT

Compositions and methods for treating and/or preventing hangover are disclosed. In certain embodiments, the compositions include at least one B vitamin, activated charcoal, at least one mineral, and at least one herbal extract.

6 Claims, No Drawings

(56) References Cited

OTHER PUBLICATIONS

Eng Abstract of KR 2006023093 A, Mar. 2006.*
Amino Acid Studies, Glutathione, http://aminoacidstudies.org/l-glutathione/, Accessed Nov. 17, 2017.
Champe et al., Lippincott's Illustrated Reviews Biochemistry, 2nd ed., Chapter 10 Hexose Monophosphate Pathway, p. 114, 1994.
Champe et al., Lippincott's Illustrated Reviews Biochemistry, 2nd ed, Chapter 28 Vitamins, pp. 321-329, 1994.
Doctors Lounge, Drug Index: Magnesium Hydroxide. http://www.doctorslounge.com/gastroenterology/drugs/antacids/magnesium.htm, Accessed Nov. 16, 2017.
Dr. Axe: Food is Medicine, Milk Thistle Benefits: Detox the Liver & Boost Glutathione, https://draxe.com/milk-thistle-benefits/, Accessed Nov. 17, 2017.
Dr. Axe: Food is Medicine, Vitamin B5/ Pantothenic Acid Deficiency & How to get enough! https://draxe.com/vitamin-b5/, Accessed Nov. 17, 2017.
Emedicinehealth: Activated Charcoal. http://www.emedicinehealth.com/activated_charcoal/page2_em.htm, Accessed Nov. 16, 2017.
Emedicinehealth: Prickly Pear Cactus. http://www.emedicinehealth.com/prickly_pear_cactus-page2/vitamins-supplements.htm, Accessed Nov. 16, 2017.
Goepp, Julius, The Overlooked Compound That Saves Lives, Life Extension Magazine, http://www.lifeextension.com/magazine/2010/5/n-acetyl-cysteine/page-01, May 2010.
Kelly, GS, Clinical Applications of N-acetylcysteine, Alternative Medicine Review, vol. 3, No. 2, pp. 114-127, Apr. 1998.
McCall et al., Function and Mechanism of Zinc Metalloenzymes, The Journal of Nutrition, vol. 130, No. 5, pp. 14375-14465, May 1, 2000.

National Institutes of Health: Office of Dietary Supplements, Zinc: Fact Sheet for Health Professionals, https://ods.od.nih.gov/factsheets/Zinc-HealthProfessional/, Accessed Nov. 17, 2017.
Shen et al., Dihydromyricetin as a Novel Anti-Alcohol Intoxication Medication, The Journal of Neuroscience, vol. 32, pp. 390-401, Jan. 2012.
University of Maryland Medical Center, Medical Reference Guide: Green Tea. http://umm.edu/health/medical/altmed/herb/green-tea, Accessed Nov. 16, 2017.
White, Brett, Ginger: An Overview, American Family Physician, vol. 75, No. 11, pp. 1689-1691, Jun. 2007.
Wikipedia: The Free Encyclopedia, *Silybum marianum*(Milk Thistle), https://en.wikipedia.org/wiki/Silybum_marianum#Medicinal_use), Accessed Nov. 16, 2017.
Leon, et al., Therapeutic Cocktail Approach for Treatment of Hyperhomocysteinemia in Alzheimer's Disease, Cell Medicine, vol. 10, pp. 1-6, 2018.
National Center for Biotechnology Information. PubChem Database. Glutathione, CID=124886, https://pubchem.ncbi.nlm.nih.gov/compound/Glutathione (accessed on Jan. 30, 2020).
National Center for Biotechnology Information. PubChem Database. Acetylcysteine, CID=12035, https://pubchem.ncbi.nlm.nih.gov/compound/Acetylcysteine (accessed on Jan. 30, 2020).
Ramen, T., Depletion of Glutathione during Oxidative Stress and Efficacy of N-Acetyl Cysteine: An Old Drug with New Approaches, Medicinal Chemistry, vol. 5, No. 1, pp. 37-39, 2015.
Goodson, A., Top 9 Benefits of NAC (N-Acetyl Cysteine), Sep. 26, 2018, https://www.healthline.com/nutrition/nac-benefits (accessed on Jan. 30, 2020).

* cited by examiner

NATURAL FORMULATION FOR TREATING HANGOVER

RELATED APPLICATIONS

This application is a continuation of U.S. application Ser. No. 15/345,143, filed Nov. 7, 2016, the contents of which are incorporated herein by reference in their entirety.

FIELD

The present embodiments relate to compositions and methods for treating hangovers. In particular, a powder comprising charcoal and a blend of vitamins, minerals and herbal supplements, in a unit dosage stick pack, is disclosed for mixing with water to form an effervescent, therapeutic liquid.

BACKGROUND

Hangovers are the result of drinking excessive alcohol. However, the amount of alcohol required to produce a hangover varies from person to person. For example, in some people, a single alcoholic drink is sufficient to trigger a hangover. The symptoms of a hangover can include nausea and vomiting, headache and muscle ache, dry mouth, fatigue and weakness, shakiness, decreased ability to concentrate, reduced sleep quality or duration, mood disturbances, thirst, and rapid heartbeat. These symptoms often arise as one's blood alcohol level returns to normal levels after an episode of drinking. If an episode of drinking occurs in the evening, the hangover symptoms typically appear the following morning.

Multiple factors can contribute to the development of a hangover. For example, alcohol has a diuretic effect that causes excess urination leading to dehydration. Dehydration in turn causes lightheadedness, dizziness, and thirst. Alcohol also irritates the stomach lining by increasing the production of acid and by delaying gastric emptying. These effects can cause nausea, vomiting, and abdominal pain. Alcoholic beverages contain substances called congeners, which can contribute to hangover symptoms. Alcohol also reduces blood sugar levels, which can cause weakness, fatigue, mood disturbances, and unsteadiness.

Hangover has generally been considered to be an insolvable problem, and there are currently no truly effective cures for hangover. It is generally believed that the only way to reliably avoid symptoms is to abstain from drinking alcohol. Thus, there has been a long-felt need for an effective solution to the problem of hangover.

SUMMARY

A composition for treating and/or preventing a hangover is disclosed. The composition includes an effective amount of at least one B vitamin, an effective amount of activated charcoal, an effective amount of a mineral, and an effective amount of at least one herbal extracts, wherein the effective amounts of the at least one B vitamin, activated charcoal, mineral, and the at least one herbal extracts are sufficient in combination to treat and/or prevent the hangover.

The composition may be in the form of a powder. The powder may be in a granulated form.

In one embodiment, the amount of each of the at least one B vitamins is in a range of about 0.01 µg to about 100 mg per unit dose of the powder.

In one embodiment, the amount of activated charcoal is in a range of about 1.0 mg to about 1000 mg per unit dose of the powder.

In one embodiment, the amount of mineral is in a range of about 1.0 mg to about 500 mg per unit dose of the powder.

In one embodiment, the amount of the at least one herbal extracts is in a range of about 10 mg to 2000 mg unit dose of the powder.

In one embodiment, the composition is an oral supplement. The oral supplement may be a capsule or a tablet or a powder.

In another embodiment, a composition for treating and/or preventing a hangover is disclosed. The composition includes the following ingredients: an effective amount of at least one herbal extract, selected from the group consisting of milk thistle, ginger root, prickly pear, *Hovenia dulcis* and green tea leaf extract; an effective amount of a mineral, selected from magnesium or zinc; an effective amount of activated charcoal; an effective amount of at least one B vitamin selected from the group consisting of B1, B2, B6, B12, niacin, pantothenic acid, biotin and folic acid; and an effective amount of at least one additional agent selected from N-Acetyl L-Cysteine or L-Glutathione; wherein the effective amounts of the ingredients are sufficient in combination to treat and/or prevent the hangover.

A method for treating and/or preventing a hangover in a subject in need thereof is disclosed in accordance with another embodiment. The method includes administering to the subject a composition comprising an effective amount of at least one B vitamin, an effective amount of at least one mineral, an effective amount of activated charcoal, and an effective amount of at least one herbal extract, wherein the effective amounts are sufficient in combination to treat and/or prevent the hangover condition.

The administering may comprise orally administering the composition in a form of a powder that is dissolved in a liquid.

In one embodiment, the amount of each of the at least one B vitamins administered is in a range of about 0.01 µg to about 100 mg per unit dose.

In one embodiment, the amount of activated charcoal administered is in a range of about 1.0 mg to about 1000 mg per unit dose.

In one embodiment, the amount of mineral administered is in a range of about 1.0 mg to about 500 mg per unit dose.

In one embodiment, the amount of the at least one herbal extracts administered is in a range of about 10 mg to 2000 mg unit dose.

In one embodiment, the administering comprises orally administering the composition in the form of an oral supplement.

In one embodiment, the administering comprises orally administering one, two, three or four doses per day.

In one embodiment, the composition comprises one or more micronutrients selected from the group consisting of vitamin A, vitamin B1, vitamin B2, vitamin B3, vitamin B5, vitamin B6, vitamin B12, vitamin C, vitamin D, vitamin E, vitamin K, Niacin, Folic Acid, Biotin, Calcium, Pantothenic Acid, Iron, Phosphorous, Iodine, Potassium, Zinc, Selenium, Manganese, Magnesium, Copper, Choline, Inositol, Omega 3, Lycopene, Lutein, Zeaxanthin, Milk Thistle, Ginger Root Extract, Prickly Pear Fruit (Stem) Concentrate, N-Acetyl L-Cysteine, *Hovenia dulcis* Fruit/Resin Extract, Green Tea Leaf Extract, and L-Glutathione.

In one embodiment, the administering comprises both topically applying a dose of the composition in the form of a topical gel or a topical cream, and orally administering a dose of the composition in the form of an oral supplement.

In some embodiments the composition further comprises one or more ingredients selected from the group consisting silicon dioxide, citric acid, stevia leaf extract, and maltodextrin.

In some embodiments, the composition comprises natural flavors such as citrus, berry, mixed berry, blackberry, blackcurrant, raspberry, blueberry, or strawberry.

In some embodiments, the composition is in the form of a powder comprising charcoal and a blend of vitamins, minerals and herbal supplements.

In some embodiments, the composition is contained in a unit dosage stick pack. In some arrangements, the contents of the stick may be dispensed into liquid and mixed to form a therapeutic liquid. In some arrangements, the therapeutic liquid can be effervescent.

In some embodiments, the composition further comprises a pharmaceutically acceptable carrier. In some embodiments, the composition is an oral supplement. In some arrangements of the composition the oral supplement is a capsule, a lozenge, a gel, a spray, a tincture, an orally dissolving strip, dissolving tablet, a tablet, liquid, or a powder.

In one particular embodiment, the composition comprises Vitamin B1, Vitamin B2, Niacin, Vitamin B6, Folic Acid, Vitamin B12, Biotin, Pantothenic Acid, Magnesium, Zinc, Milk Thistle Whole Plant, Ginger Root Extract, Prickly Pear Fruit (Stem) Concentrate, N-Acetyl-L-Cysteine, activated charcoal, *Hovenia dulcis* Fruit/Resin Extract, Green Tea Leaf Extract, and L-Glutathione. In some arrangements, the composition further comprises silicon dioxide, natural flavors, citric acid, and stevia leaf extract.

A method for treating and/or preventing hangover symptoms in a subject in need thereof is provided. The method comprises administering to the subject a composition comprising an effective amount of vitamins, such as B vitamins, and an effective amount of minerals, such as magnesium, in amounts sufficient to treat and/or prevent the hangover symptoms. In some embodiments, the method further comprises administering effective amounts of herbal extracts and/or activated charcoal. In some embodiments of the method, administering comprises orally administering the composition.

In some embodiments of the method, the composition administered is administered in a single dose. In other embodiments of the method, the composition administered is administered in multiple doses.

In some embodiments of the method, administering comprises dissolving the composition in the form of a powder in liquid and orally administering the composition and liquid mixture to a subject. In other arrangements, administering comprises dissolving the composition in the form of a tablet in liquid and orally administering the composition and liquid mixture to a subject. In some embodiments, administering comprises administering a capsule containing the composition to a subject, which the subject then swallows. In other arrangements, administering comprises orally administering the composition in the form of a gel to a subject.

In some embodiments of the method, the amount of Vitamin B1 administered is in a range of about 0.1 mg to about 1 mg per unit dosage form. In some arrangements of the method, the composition administered comprises Vitamin B1 from Thiamine HCL.

In some embodiments of the method, the amount of Vitamin B2 administered is in a range of about 0.1 mg to about 1 mg per unit dosage form. In some arrangements of the method, the composition administered comprises Vitamin B2 in the form of Riboflavin.

In some embodiments of the method, the amount of Niacin administered is in a range of about 1 mg to about 100 mg per unit dosage form.

In some embodiments of the method, the amount of Vitamin B6 administered is in a range of about 0.1 mg to about 10 mg per unit dosage form. In some arrangements of the method, the composition administered comprises Vitamin B6 from Pyridoxine HCL.

In some embodiments of the method, the amount of Folic Acid administered is in a range of about 0.1 mcg to about 100 mcg per unit dosage form.

In some embodiments of the method, the amount of Vitamin B12 administered is in a range of about 0.1 µg to about 10 µg per unit dosage form. In some arrangements of the method, the composition administered comprises Vitamin B12 in the form of Cyanocobalamin.

In some embodiments of the method, the amount of Biotin administered is in a range of about 10 µg to about 500 µg per unit dosage form.

In some embodiments of the method, the amount of Pantothenic Acid administered is in a range of about 0.5 mg to about 50 mg per unit dosage form. In some embodiments of the method, the composition administered comprises Pantothenic Acid from Calcium D-Pantothenate.

In some embodiments of the method, the amount of Magnesium administered is in a range of about 10 mg to about 1000 mg per unit dosage form. In some arrangements of the method, the composition administered comprises Magnesium from Magnesium Oxide. However, in other arrangements, the Magnesium in the composition administered may be from magnesium citrate, magnesium chloride, magnesium oxide or some other form of magnesium.

In some embodiments of the method, the amount of Zinc administered is in a range of about 1 mg to about 100 mg per unit dosage form. In some arrangements of the method, the composition administered comprises Zinc from Zinc Oxide.

In some embodiments of the method, the amount of Milk Thistle administered is in a range of about 100 mg to about 2000 mg per unit dosage form.

In some embodiments of the method, the amount of Ginger Root Extract administered is in a range of about 50 mg to about 1000 mg per unit dosage form. In some arrangements of the method, the composition administered comprises Ginger Root Extract in the form of 5% Gingerols.

In some embodiments of the method, the amount of Prickly Pear Fruit (Stem) Concentrate administered is in a range of about 50 mg to about 1000 mg per unit dosage form. In some arrangements of the method, the composition administered comprises Prickly Pear Fruit (Stem) Concentrate in the form of stem concentrate 20:1.

In some embodiments of the method, the amount of N-Acetyl-L-Cysteine administered is in a range of about 50 mg to about 500 mg per unit dosage form.

In some embodiments of the method, the amount of activated charcoal administered is in a range of about 50 mg to about 500 mg per unit dosage form. In some embodiments, NORIT® brand activated charcoal is used.

In some embodiments of the method, the amount of *Hovenia dulcis* Fruit/Resin Extract administered is in a range of about 10 mg to about 1000 mg per unit dosage form. In some arrangements of the method, the composition administered comprises *Hovenia dulcis* Fruit/Resin Extract 10:1.

In some embodiments of the method, the amount of Green Tea Leaf Extract administered is in a range of about 10 mg to about 500 mg per unit dosage form.

In some embodiments of the method, the amount of L-Glutathione administered is in a range of about 5 mg to about 100 mg per unit dosage form.

In some embodiments of the method, the composition administered further comprises one or more ingredients selected from the group consisting silicon dioxide, citric acid, stevia leaf extract, and maltodextrin.

In some embodiments of the method, the composition administered comprises natural flavors such as berry, mixed berry, blackberry, blackcurrant, raspberry, blueberry, or strawberry.

In some embodiments of the method, the composition administered further comprises one or more micronutrients selected from the group consisting of vitamin A, vitamin B1, vitamin B2, vitamin B3, vitamin B5, vitamin B6, vitamin B12, vitamin C, vitamin D, vitamin E, vitamin K, Niacin, Folic Acid, Biotin, Calcium, Pantothenic Acid, Iron, Phosphorous, Iodine, Potassium, Zinc, Selenium, Manganese, Magnesium, Copper, Choline, Inositol, Omega 3, Lycopene, Lutein, Zeaxanthin, Milk Thistle, Ginger Root Extract, Prickly Pear Fruit Concentrate, N-Acetyl-L-Cysteine, *Hovenia dulcis* Fruit/Resin Extract, Green Tea Leaf Extract, and L-Glutathione.

In one particular embodiment of the method, a composition in powder form comprising Vitamin B1, Vitamin B2, Niacin, Vitamin B6, Folic Acid, Vitamin B12, Biotin, Pantothenic Acid, Magnesium, Zinc, Milk Thistle Whole Plant, Ginger Root Extract, Prickly Pear Fruit (Stem) Concentrate, N-Acetyl-L-Cysteine, Activated Charcoal, *Hovenia dulcis* Fruit/Resin Extract, Green Tea Leaf Extract, and L-Glutathione is orally administered after mixing in a liquid.

DETAILED DESCRIPTION

Embodiments of this disclosure relate generally to the use of vitamins, minerals, activated charcoal, and herbal extracts in combination for the prevention and treatment of hangover. The combination therapy may include oral delivery.

Unless specified otherwise, the amounts of each ingredient are expressed as weight (e.g., mg or mcg (rig)) per unit dosage form (e.g., 2 to 4.5 grams powdered or granulated ingredients in e.g., tall stick packages or square foil packages). The unit dosage is that amount of the composition formulated for a single dose/serving.

Vitamins

In certain embodiments, the composition for treating or preventing hangover include B vitamins. The B vitamins act as antioxidants and coenzymes that serve important roles in energy metabolism, nervous system health, digestive health, skin health, and proper function of the immune system. B vitamins can aid in boosting energy and mood, facilitating concentration, fighting stress, and decreasing symptoms such as nausea and vomiting. Deficiencies of the B vitamins are frequently seen in acute alcohol use and chronic alcoholism.

More particularly, the B vitamins of the composition include Vitamin B1. Vitamin B1 (thiamine) is generally known to support nerve and brain health, to promote gut health, to increase energy, and to combat the symptoms of stress. Vitamin B1 is required to form adenosine triphosphate, which serves as the source of energy for all cells. Deficiency of Vitamin B1 can include nausea, headache, fatigue, abdominal discomfort, depression, and irritability.

Another B vitamin includes thiamine pyrophosphate. Thiamine pyrophosphate serves as a coenzyme in the oxidative decarboxylation of alpha keto acids, and in the formation or degradation of alpha ketols by transketolase. The oxidative decarboxylation of pyruvate and alpha ketoglutarate plays a key role in energy metabolism of most cells, but is particularly important in tissues of the nervous system. In thiamine deficiency the activity of these two dehydrogenase reactions is decreased, resulting in a decreased production of ATP, and thus impaired cellular function. In the United States, thiamine deficiency is seen primarily in association with chronic alcoholism and is due to dietary insufficiency or impaired intestinal absorption of the vitamin. Some alcoholics develop the Wernicke-Korsakoff syndrome, a deficiency state characterized by apathy, loss of memory, and a rhythmical to-and-fro motion of the eyes. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 321-2.).

Vitamin B2 (riboflavin) promotes energy production, serves as an antioxidant, and plays a role in red blood cell production. Symptoms of Vitamin B2 deficiency can include digestive problems, fatigue, sensitivity to light, eye fatigue, and cracks and sores at the corners of the mouth. The two biologically active forms are flavin mono nucleotide (FMN) and flavin adenine dinucleotide (FAD) formed by the transfer of an AMP moiety from ATP to FMN. FMN and FAD are each capable of reversibly accepting two hydrogen atoms, forming FMNH2 or FADh2. FMN and FAD are bound tightly—sometimes covalently—to flavoenzymes that catalyze the oxidation or reduction of a substrate. Riboflavin deficiency is not associated with a major human disease, although it frequently accompanies other vitamin deficiencies. Deficiency symptoms include dermatitis, cheilosis, and glossitis. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 322-3.).

Vitamin B3 (niacin) helps promote energy production, serves as an antioxidant, improves circulation, and suppresses inflammation. Symptoms of Vitamin B3 deficiency can include fatigue, vomiting, depression, poor circulation, and indigestion. In more severe cases, Vitamin B3 can cause a constellation of symptoms including diarrhea, dementia, and cracked scaly skin, which is known as pellagra. Pellagra is a disease involving the skin, GI tract, and central nervous system. The symptoms of pellagra progress through the three Ds: Dermatitis, Diarrhea, Dementia, and if untreated, death.

Niacin, or nicotinic acid, is a substituted pyridine derivative. The biologically active coenzyme forms are nicotinamide adenine dinucleotide (NAD+) and its phosphorylated derivative, nicotinamide adenine dinucleotide phosphate (NADP+). Nicotinamide, a derivative of nicotinic acid that contains an amide instead of a of a carboxyl group, also occurs in the diet. Nicotinamide is readily dominated in the body and therefore is nutritionally equivalent to nicotinic acid. NAD+ and NADP+ serve as coenzymes in oxidation-reduction reactions in which the coenzyme undergoes reduction of the pyridine ring by accepting a hydride ion (hydrogen atom plus one electron. The reduced forms of NAD+ and NADP+ are NADH and NADPH, respectively (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 323-4.).

Vitamin B5 (pantothenic acid from Calcium D-Pantothenate) plays a role in carbohydrate and fat metabolism, red blood cell production, and the production of sex and stress hormones. It also plays a role in maintaining digestive tract health. Deficiencies of Vitamin B5 can lead to symptoms such as fatigue, vomiting, depression, irritability, stomach pain, insomnia, and upper respiratory infections. Pantothenic acid is important for our bodies to properly use carbohydrates, proteins, and lipids and for healthy skin e.g. energy production & fat metabolism e.g. improves cardiovascular health, synthesizes cholesterol, metabolizes food into energy, maintains healthy nerve function, improves mental performance, helps control the body's stress response, helps wound healing. helps with rheumatoid arthritis, aids in immune function, helps fight acne and protect skin health. (https://draxe.com/vitamin-b5/). Pantothenic acid is a component of coenzyme A, which functions in the transfer of acyl groups. Coenzyme A contains a thiol group that carries acyl compounds as activated thiol esters. Examples of such structures are succinyl CoA, fatty acyl CoA, and acetyl CoA. Pantothenic acid is also a component of fatty acid synthase. Pantothenic acid deficiency is not well characterized in humans. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 324-5.)

Vitamin B6 (pyridoxine) plays an important role in nervous system development and functioning. It is also essential to red blood cell production and immune function. Deficiencies can cause nervousness, irritability, muscle weakness, difficulty concentrating, depression, and short term memory loss. Vitamin B6 is a collective term for pyridoxine, pyridoxal, and pyridoxine, all derivatives of pyridine, differing only in the functional group attached to the ring. Pyridoxine occurs primarily in plants, whereas pyridoxal and pyridoxamine are found in foods obtained from animals. All three compounds can serve as precursors of the biologically active coenzyme, pyridoxal phosphate. Pyridoxal phosphate functions as a coenzyme for a large number of enzymes, particularly those that catalyze reactions involving amino acids. Isoniazid, a drug frequently used to treat tuberculosis, can induce a B6 deficiency by forming an inactive derivative with pyridoxal phosphate. Dietary supplementation with B6 is thus an adjunct to isoniazid treatment. Otherwise, dietary deficiencies in pyridoxine are rare but have been observed in newborn infants fed formulas low in vitamin B6, women taking oral contraceptives, and in alcoholics. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 328-9.)

Vitamin B7 (biotin) helps regulate blood sugar and plays a role in maintenance of the nervous system and key metabolic processes. Deficiencies can cause fatigue, muscle pain, dermatitis, dry skin, and intestinal dysfunction. Biotin is a coenzyme in carboxylation reactions, in which it serves as a carrier of activated carbon dioxide. Biotin is covalently bound to the epsilon-amino groups of lysine residues of biotin dependent enzymes. Biotin deficiency does not occur naturally because the vitamin is widely distributed in food. Also, a large percentage of the biotin requirement in humans is supplied by intestinal bacteria. However, the addition of raw egg-white to the diet as a source of protein induces symptoms of biotin deficiency, namely dermatitis, glossitis, loss of appetite, and nausea. Raw egg white contains a glycoprotein, avidin, which tightly binds biotin and prevents its absorption from the intestine. However, with a normal diet, it has been estimated that 20 eggs per day would be required to induce a deficiency syndrome. Thus, inclusion of an occasional raw egg in the diet does not lead to biotin deficiency. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 324-5.)

Vitamin B9 (folic acid) aids in fat metabolism and promotes healthy liver, skin, eye, and nervous system function. Deficiencies of Vitamin B9 can cause irritability, diarrhea, loss of mental acuity, forgetfulness, and loss of appetite. Folic acid (or folate) plays a key role in one-carbon metabolism, and is essential for the biosynthesis of the purines and the pyrimidine, thymine. Folic acid deficiency is probably the most common vitamin deficiency in the United States, particularly among pregnant women and alcoholics. Folic acid is composed of a pterin ring attached to p-aminobenzoic acid (PABA) and conjugated with one or more glutamic acid residues. Humans cannot synthesize PABA or attach the first glutamic acid. The biologically active form of folic acid is tetrahydrofolic acid (THF), which is produced by the two-step reduction of folate by dihydrofolate reductase (DHF). THF receives one-carbon fragments from donors such as serine, glycine, and histidine and transfers them to intermediates in the synthesis of amino acids, purines, and thymidine—the characteristic pyrimidine of DNA. Folic acid deficiency is characterized by growth failure and megaloblastic anemia. The anemia is a result of diminished DNA synthesis in erythropoietic stem cells, a process that requires tetrahydrofolate derivatives. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 325-6.)

Vitamin B12 (Cyanocobalamin) is required in humans for two essential enzymatic reactions: the synthesis of methionine and the isomerization of methylmalonyl CoA that arises from fatty acids with odd numbers of carbon atoms. When the vitamin is deficient, abnormal fatty acids accumulate and become incorporated into the cell membranes, including those of the nervous system. This may account for some of the neurologic manifestations of vitamin B12 deficiency. Cobalamin contains a corrin ring system that differs from the porphyrins in that two of the pyrrole rings are linked directly rather than through a methane bridge. Cobalt is held in the center of the corrin ring by four coordination bonds from the nitrogens of the pyrrole groups. The remaining coordination bonds of the cobalt are with the nitrogen of 5,6-dimethylbenzimidazole and with cyanide in commercial preparations of the vitamin in the form of cyanocobalamin. The coenzyme forms of cobalamin are 5' deoxyadenosylcobalamin, in which cyanide is replaced with 5'deoxyadenosine and methylcobalamin, in which cyanide is replaced by a methyl group.

The effects of cobalamin deficiency are most pronounced in rapidly diving cells such as the erythropoietic tissue of bone marrow and the mucosal cells of the intestines. In contrast to other water-soluble vitamins, significant amounts of vitamin B12 are stored in the body. As a result, it may take several years for the clinical symptoms of B12 deficiency to develop in individuals who have had a partial or total gastrectomy (who therefore become intrinsic factor-deficient) and can no longer absorb the vitamin. (Champe, Pamela C. & Harvey, Richard A. Lippincott's Illustrated Reviews Biochemistry. 2nd ed. Philadelphia: Lippincott Williams & Wilkins; c1994. Chapter 28 Vitamins; p 326-8.)

Minerals

In addition to the above-summarized B vitamins, minerals are also included in certain embodiments of the composition. Magnesium is one useful mineral in the composition. It helps promote normal nerve and muscle function while supporting the immune system, cardiac function, and the integrity of bones. It also helps regulate blood sugar levels. Magnesium deficiency can cause symptoms such as fatigue, insomnia, anorexia, confusion, irritability, muscle twitching, and poor memory. Magnesium has two mechanisms of action: 1) Antacid (magnesium hydroxide, magnesium oxide): neutralizes or reduces gastric acidity, resulting in an increase in the pH of the stomach and duodenal bulb and inhibition of the proteolytic activity of pepsin. 2) Laxative (magnesium citrate, magnesium hydroxide): attracts/retains water in intestinal lumen and distends bowel; causes the duodenal secretion of cholecystokinin, which stimulates fluid secretion and intestinal motility.

Zinc is another useful mineral. Zinc (from Zinc Oxide) is involved in numerous aspects of cellular metabolism, namely boosts immune system, blood function, and enhances the action of insulin. It is required for the catalytic activity of hundreds of enzymes and it plays a role in immune function, protein synthesis, wound healing, DNA synthesis, and cell division. Zinc also supports normal growth and development during pregnancy, childhood, and adolescence and is required for proper sense of taste and smell. A daily intake of zinc is required to maintain a steady state because the body has no specialized zinc storage system. (https://ods.od.nih.gov/factsheets/Zinc-Health Professional/)

Zinc is required for the activity of >300 enzymes, covering all six classes of enzymes. Zinc binding sites in proteins are often distorted tetrahedral or trigonal bipyramidal geometry, made up of the sulfur of cysteine, the nitrogen of histidine or the oxygen of aspartate and glutamate, or a combination. Zinc in proteins can either participate directly in chemical catalysis or be important for maintaining protein structure and stability. In all catalytic sites, the zinc ion functions as a Lewis acid. (http://jn.nutrition.org/content/130/5/1437S.full)

Zinc deficiency is characterized by growth retardation, loss of appetite, and impaired immune function. In more severe cases, zinc deficiency causes hair loss, diarrhea, delayed sexual maturation, impotence, hypogonadism in males, and eye and skin lesions. Weight loss, delayed healing of wounds, taste abnormalities, and mental lethargy can also occur. Approximately 30%-50% of alcoholics have low zinc status because ethanol consumption decreases intestinal absorption of zinc and increases urinary zinc excretion. In addition, the variety and amount of food consumed by many alcoholics is limited, leading to inadequate zinc intake. (https://ods.od.nih.gov/factsheets/Zinc-HealthProfessional/)

Activated Charcoal

In addition to the B vitamins and minerals, activated charcoal may also be included in certain embodiments of the composition. Activated charcoal is charcoal that has been treated in the presence of a gas that causes the charcoal to increase its ability to adsorb substances from its surroundings. The adsorptive power of activated charcoal is due to its many pores that allow it to act as a sponge for toxins and other substances. NORIT® brand activated charcoal is commonly given in the emergency room setting and involves the administration of more than 2 doses of oral activated charcoal to enhance elimination of drugs ingested in acute poisoning. The rationale is that charcoal interrupts the enteroenteric, enterogastric, and enterohepatic circulation of absorbed drugs, whereas unabsorbed drugs will be adsorbed to activated charcoal. The charcoal is prepared from vegetable matter such as peat, wood, coal, or coconut shell. It is then activated by high heat in oxidizing gas, such as steam or carbon dioxide, that increases its surface area to at least 900 $m^2/g$ to meet industry standards.

NORIT® brand activated charcoal binds to dangerous toxins so that they can be safely eliminated. More particularly, activated charcoal adsorbs a wide variety of drugs and chemicals. Adsorption is a process in which atoms and molecules move from a bulk phase (such as a solid, liquid, or gas) onto a solid or liquid surface. In other words, the toxic substance attaches to the surface of the charcoal. Because charcoal is not "digested," it stays inside the GI tract and eliminates the toxin when the person has a bowel movement.

This mechanism of action should not be confused with absorption. Absorption occurs when a substance passes into or through a tissue, like water passing into a sponge. Once the chemical or drug has been absorbed by the GI tract, activated charcoal can no longer retrieve the toxic ingestion. It will only attach to substances that are still inside the stomach or intestines. The charcoal is "activated" because it is produced to have a very fine particle size. This increases the overall surface area and adsorptive capacity of the charcoal. It is produced by adding acid and steam to carbonaceous materials such as wood, coal, rye starch, or coconut shells. To put this in perspective, one standard 50-gram dose of activated charcoal has the surface area of 10 football fields. While activated charcoal does not adsorb alcohol, it does help quickly remove other toxins from the body that contribute to poisoning. Alcohol is rarely consumed in its pure form; mixers that include artificial sweeteners and chemicals are common. Activated charcoal removes these toxins.

Herbal Extracts

Besides the B vitamins, minerals and activated charcoal, herbal extracts including plant materials and extracts may also show efficacy in treating and/or preventing hangover. For example, Milk Thistle Whole Plant helps support liver health and get rid of toxins. Milk thistle has been used for over 2,000 years. The plant is native to the Mediterranean region and a member of the Asteraceae plant family, which also includes other plants like sunflowers and daisies. The Greek physician and botanist Dioscorides was the first to describe milk thistle's healing properties back in the year 40 A.D. Milk thistle benefits work by drawing toxins out of the body that can cause a range of symptoms and diseases-including cancer development, high cholesterol, diabetes, kidney stones, gall bladder disorders, negative effects of chemotherapy, alcohol use, skin damage and much more.

As an antioxidant, milk thistle is equally powerful to other important nutrients like vitamin E or vitamin C, which help fight free radical damage and slow the aging process that can lead to disease development. It specifically contains high levels of lipophilic extracts from the seeds of the plant, which act as bioflavonoid antioxidants that increase immunity and slow down oxidative stress. While it has many different benefits, milk thistle is most well-known for being a natural liver supporter and detoxifier. The liver constantly works hard to help defend us from toxins that are common in our everyday life, acting like a filter and removing harmful substances from the body. (https://draxe.com/milk-thistle-benefits/)

Silymarin, the active ingredient in milk thistle, is an antioxidant that can protect against depletion of glutathione, which is a "master antioxidant" that's extremely useful at helping prevent disease formation. Glutathione is found naturally in the human body, as well as in some plants, mushrooms, fungus and algae. Its biggest role is to help fight oxidative stress that leads to such diseases as cancer, diabetes, heart disease and neurodegenerative diseases. It can help prevent damage to important cellular components caused by reactive oxygen species, such as free radicals. One of the biggest milk thistle benefits is that it preserves glutathione. In the modern American diet, pollution, toxins, medications, stress, trauma, aging, infections and radiation all work to deplete liver capabilities and also glutathione in the body. Milk thistle helps increase glutathione levels by improving liver detox functions. Milk thistle strengthens the liver cell membranes, buffering them from invading toxins, and supports liver regeneration and glutathione formation. (https://draxe.com/milk-thistle-benefits/)

Milk thistle has been used for a number of purposes including liver disease, and cancer; however, clinical studies are largely heterogeneous and contradictory. In trials, silymarin has typically been administered in amounts ranging from 420-480 mg per day in two to three divided doses. However, higher doses have been studied, such as 600 mg daily in the treatment of type II diabetes (with significant results). (https://en.wikipedia.org/wiki/Silybum_marianum#Medicinal_use)

Another natural, plant-based antioxidant that may be included in certain embodiments is Ginger Root Extract (5% Gingerols). Ginger Root Extract serves as an antioxidant, helps the digestive system, and can ease nausea and vomiting. The exact mechanism of action of ginger in relation to its antiemetic properties is unclear, although it appears to inhibit serotonin receptors and to exert antiemetic effects at the level of the gastrointestinal system and in the central nervous system. 1 In relation to its potential anti-inflammatory properties, ginger extract has been shown to inhibit the activation of tumor necrosis factor α and cyclooxygenase-2 expression during in vitro studies of human synoviocytes.

Another natural, plant-based antioxidant is Prickly Pear Fruit (Stem) Concentrate, which serves as an antioxidant, an anti-inflammatory, and an antiviral while facilitating energy production, nerve & muscle function, and insulin regulation. Used in Native American and Spanish American cultures as a hangover treatment. Prickly pear cactus contains fiber and pectin, which can lower blood glucose by decreasing the absorption of sugar in the stomach and intestine. Some researchers think that it might also decrease cholesterol levels, and kill viruses in the body.

Green Tea Leaf Extract (80% Caffeine) improves mental alertness and thinking, helps with vomiting, diarrhea, headaches, helps the liver detoxify. Tea has been cultivated for centuries, beginning in India and China. Today, tea is the most widely-consumed beverage in the world, second only to water. Hundreds of millions of people drink tea, and studies suggest that green tea (*Camellia sinensis*) in particular has many health benefits. There are 3 main varieties of tea, green, black, and oolong. The difference is in how the teas are processed. Green tea is made from unfermented leaves and reportedly contains the highest concentration of powerful antioxidants called polyphenols. Antioxidants are substances that fight free radicals, damaging compounds in the body that change cells, damage DNA, and even cause cell death. Many scientists believe that free radicals contribute to the aging process, as well as the development of a number of health problems, including cancer and heart disease. Antioxidants, such as polyphenols in green tea, can neutralize free radicals and may reduce or even help prevent some of the damage they cause.

In traditional Chinese and Indian medicine, practitioners used green tea as a stimulant, a diuretic (to help rid the body of excess fluid), an astringent (to control bleeding and help heal wounds), and to improve heart health. Other traditional uses of green tea include treating gas, regulating body temperature and blood sugar, promoting digestion, and improving mental processes. Green tea has been extensively studied in people, animals, and laboratory experiments. Population-based studies have shown that men who drink more than 10 cups of green tea per day are less likely to develop liver problems. Green tea also seems to protect the liver from the damaging effects of toxic substances such as alcohol. Animal studies have shown that green tea helps protect against liver tumors in mice. Results from several animal and human studies suggest that plant chemicals in green tea called catechins, may help treat viral hepatitis, an inflammation of the liver. (http://umm.edu/health/medical/altmed/herb/green-tea)

*Hovenia dulcis* Fruit/Resin Extract 10:1 accelerates detoxification of ethanol, and possess hepatoprotective, antioxidative, antimicrobial and antidiabetic properties. Used in Asian cultures as a hangover treatment. Dihydromyricetin (DHM, 1 mg/kg, i.p. injection), a flavonoid component of herbal medicines, counteracted acute alcohol (EtOH) intoxication, and also withdrawal signs in rats including tolerance, increased anxiety and seizure susceptibility; DHM greatly reduced EtOH consumption in an intermittent voluntary EtOH intake paradigm in rats.

Other Ingredients

N-Acetyl L-Cysteine prevents alcoholic liver damage and is used in the treatment of some overdoses and poisonings. N-Acetyl L-Cysteine, the acetylated variant of the amino acid L-cysteine, is an excellent source of sulfhydryl (SH) groups, and is converted in the body into metabolites capable of stimulating glutathione (GSH) synthesis, promoting detoxification, and acting directly as free radical scavengers. NAC replenishes intracellular levels of the of one of the body's most powerful antioxidant defenses glutathione (GSH), helping to restore cells' ability to fight damage from reactive oxygen species (ROS) Administration of NAC has historically been as a mucolytic agent in a variety of respiratory illnesses; however, it appears to also have beneficial effects in conditions characterized by decreased GSH or oxidative stress, such as HIV infection, cancer, heart disease, and cigarette smoking. An 18-dose oral course of NAC is currently the mainstay of treatment for acetaminophen-induced hepatotoxicity. N-Acetyl L-Cysteine also appears to have some clinical usefulness as a chelating agent in the treatment of acute heavy metal poisoning, both as an agent capable of protecting the liver and kidney from damage and as an intervention to enhance elimination of the metals.

L-Glutathione is another antioxidant that may be included in certain embodiments. Besides its role as an antioxidant, L-Glutathione is also known to enhance immune function and liver health, boost energy, and help break down acetaldehyde into harmless acetate. L-Glutathione levels are low in alcoholics. Reduced glutathione, a tripeptide-thiol (Gamma-glutamyl-cysteinyl-glycine), which is present in most cells, can chemically detoxify hydrogen peroxide. This reaction, catalyzed by glutathione peroxidase, forms oxidized glutathione, which no longer has protective properties. The cell regenerates reduced glutathione in a reaction catalyzed by glutathione reductase using NADPH as a source of reducing electrons. Thus, NADPH indirectly provides electrons for the reduction of hydrogen peroxide. Additional enzymes catalyze the conversion of other toxic oxygen intermediates to harmless products. As a group, these enzymes serve as a defense system to guard against the toxic effects of reactive oxygen intermediates. (Champe, Pamela C. & Harvey, Richard A. Lippincott's Illustrated Reviews Biochemistry. 2nd ed. Philadelphia: Lippincott Williams & Wilkins; c1994. Chapter 10 Hexose Monophosphate Pathway; p 114.)

Glutathione is an intracellular antioxidant, which acts inside the cells. As such it is able to maintain their health and performance and resist disease by neutralizing free radicals and keeping other antioxidants, including Vitamin C and E, in their active form. It also helps the liver to process toxins, helps with DNA and protein synthesis, and regulates both the nitric oxide cycle and the metabolism of iron. (http://aminoacidstudies.org/I-glutathione/)

The $GABA_A$ receptor ($GABA_AR$) is an ionotropic receptor and ligand-gated ion channel. Its endogenous ligand is γ-aminobutyric acid (GABA), the major inhibitory neurotransmitter in the central nervous system. Upon activation, the GAB AA receptor selectively conducts Cl— through its pore, resulting in hyperpolarization of the neuron. This causes an inhibitory effect on neurotransmission by diminishing the chance of a successful action potential occurring. The net effect is typically inhibitory, reducing the activity of the neuron. The $GABA_AR$'s are major targets of acute and chronic EtOH actions on the brain. At the cellular levels, DHM (1 μM) antagonized both acute EtOH-induced potentiation of $GABA_AR$'s and EtOH exposure/withdrawal-induced $GABA_AR$ plasticity, including alterations in responsiveness of extra- and post-synaptic $GABA_AR$'s to acute EtOH, and most importantly, increases in $GABA_AR$ α4 subunit expression in hippocampus and cultured neurons. DHM anti-alcohol effects on both behavior and CNS neurons were antagonized by flumazenil (10 mg/kg in vivo, 10 μM in vitro), the benzodiazepine (BZ) antagonist. DHM competitively inhibited BZ-site [3H]flunitrazepam binding (IC50, 4.36 μM), suggesting DHM interaction with EtOH involves the BZ-sites on $GABA_AR$ s. In summary, we determined DHM anti-alcoholic effects on animal models, and determined a major molecular target and cellular mechanism of DHM for counteracting alcohol intoxication and dependence. We demonstrated pharmacological properties of DHM consistent with those expected to underlie successful medical treatment of AUD; therefore, DHM is a therapeutic candidate.

Sweetening ingredients well known in the art, such as maltodextrin and artificial sweeteners, may be used in certain embodiments. In some embodiments of the composition and method, the composition administered further comprises one or more ingredients selected from the group consisting silicon dioxide, citric acid, stevia leaf extract, and maltodextrin. Likewise, flavoring ingredients well known in the art, such as citrus and berry flavoring, may be used in certain embodiments. In some embodiments of the composition and method, the composition administered comprises natural flavors such as mixed berry, blackberry, blackcurrant, raspberry, blueberry, or strawberry.

Examples

The following non-limiting examples show Volunteers' experiences with various doses and frequencies of natural formulations (Batches) of vitamins, minerals, activated charcoal, and herbal extracts, which are described below as Batches 1, 2, 3, 4, and 5. The ingredients in each batch are summarized in Table 1 below:

TABLE 1

| INGREDIENT | BATCH 1 (mg*/4.5 g serving**) | BATCH 2 (mg*/4.5 g serving**) | BATCH 3 (mg*/2 g serving**) | BATCH 4 (mg*/2 g serving**) | BATCH 5 (mg*/3 g serving**) |
|---|---|---|---|---|---|
| Milk Thistle Whole Plant | 1000.00 | 1000.00 | 444.44 | 575.75 | 863.62 |
| Magnesium (Magnesium Oxide) | 138.00 | 138.00 | 35.57 | 35.57 | 53.36 |
| Zinc (Zinc Oxide) | 9.38 | 9.38 | 3.33 | 4.17 | 5.00 |
| Ginger Root Extract | 500.00 | 500.00 | 222.22 | 222.22 | 333.33 |
| Prickly Pear Fruit Concentrate 20:1 | 500.00 | 500.00 | 222.22 | 222.22 | 333.33 |
| *Hovenia Dulcis* Fruit Extract 10:1 | 250.00 | 250.00 | 111.11 | 111.11 | 166.67 |
| Niacin | 11.08 | 11.08 | 4.48 | 4.48 | 6.72 |
| Vitamin B1 (Thiamine HCL) | 0.95 | 0.95 | 0.33 | 0.33 | 0.50 |
| Vitamin B2 (Riboflavin) | 0.91 | 0.91 | 0.38 | 0.38 | 0.57 |
| Vitamin B6 (Pyridoxine HCL) | 1.26 | 1.26 | 0.44 | 0.44 | 0.66 |
| Vitamin B12 (Cyanocobalamin) | 0.32 mcg | 0.32 mcg | 1.33 mcg | 1.33 mcg | 2.00 mcg |
| Biotin | 157.50 mcg | 157.50 mcg | 66.67 mcg | 66.67 mcg | 100.00 mcg |
| Folic Acid | 0.23 mcg | 0.23 mcg | 9.17 mcg | 9.17 mcg | 13.76 mcg |
| Pantothenic Acid (Calcium D-Pantothenate) | — | — | 2.41 | 2.22 | 3.33 |
| N-Acetyl L-Cysteine | — | — | 220.00 | 220.00 | 330.00 |
| Norit ® Activated Carbon | 250.00 | 250.00 | 111.11 | 111.11 | 166.67 |
| L-Glutathione | 50.00 | 50.00 | 22.22 | 22.22 | 33.33 |
| Maltodextrin | 1002.00 | 1002.00 | 156.30 | 131.30 | 131.30 |
| Green Tea Leaf Extract | — | 100.00 | 44.44 | 44.44 | 66.67 |
| Flavoring | *citrus* | *citrus* | berry | berry+ | berry+ |

*all units are mg per serving, except Vitamin B12, Biotin and Folic Acid, which are in mcg (μg) per serving.
**a serving mixed in 8, 10 or 12 oz of water to taste Dosing varied as described in greater detail below.

Batch 1 (citrus flavored) was the original theoretical formula brought to manufacture and was tested at 4.5 g mixed in 8, 10 or 12 ounces of water (to taste) three times per day (before drinking, during drinking, and after drinking) to prevent hangover, abate drunkenness, and maintain sobriety. This dose and frequency of Batch 1 formulation was very effective. Indeed, some case studies reported an inability to either get drunk or maintain their buzz. Many did not want to spend money on going out and drinking alcoholic beverages, and not be able to experience or maintain an alcohol buzz. Without changing the dose of 4.5 g mixed in 8, 10 or 12 oz, the frequency of administration was reduced to only two times per day (before drinking and after drinking) with similar results. The frequency was again reduced to only one time per day (after drinking). Case studies reported that this dose was very effective in preventing and treating hangover symptoms, while still allowing the desired enjoyment of the alcohol. Now the goal was to reduce further to determine the minimum efficacious dose with the requested convenience of once per day dosing (after drinking, either at end of night before bed or immediately upon rising in the morning).

Batch 2 (citrus flavored) was a similar formulation as Batch 1, with the addition of green tea leaf extract. Further, the ingredients were provided in granulated form to improve flow during packaging and dispensing. This allowed for the use of tall stick packaging instead of square packaging. The tall stick packaging was received better, aesthetically, over the square foil pack in the test group. Different unit dosage amounts were tested, including 2 and 4.5 g unit dosage amounts of the formulation from Table 1, again mixed in 8, 10 or 12 oz to taste, and given once per day (after drinking). Study participants reported that the 2 g dose was better than their usual alternative (Advil, etc.), but noticeably less effective than the 4.5 g dose (based on overall improvement and time to improvement). When administered at 4.5 g, the prophylactic and therapeutic effects observed by volunteers were similar to those reported in the Batch 1 testing described above.

Batch 3 (berry) was similar to the formulation of Batch 2 with berry flavor substituted for citrus to compare which flavor was more popular. Berry flavor was preferred to citrus. In addition, Batch 3 also included calcium D pantothenate (vitamin B5), so that all eight B vitamins (B complex) were in the formula. In addition, N-Acetyl L-Cysteine was also added to the Batch 3 formulation, to further help protect the liver. Batch 3 was tested at 2.5 g unit dose.

For Batch 4, unit dosage amounts of 2.5 and 3 g were tested of the formulation from Table 1, again mixed in 8, 10 or 12 oz to taste, and given once per day (after drinking). Efficacy in treating hangover symptoms increased in a dose-responsive manner from 2.5 to 3 g. However, based on the groups' response to earlier batches, the dose responsive increase in effectiveness seemed to plateau after 3 g, with little to no further increase in efficacy noted in the study group. Therefore, 3 g became the unit dosage amount (serving size) for further studies and was to be mixed with eight to twelve ounces of water to taste. The Batch 4 (berry) was a similar formulation as Batch 3 but had an increase berry flavoring for enhanced palatability, based on test group suggestions. Several other minor changes in this batch were also made to further refine the formula and to help in cost efficiency without sacrificing efficacy. These changes were a increase in milk thistle, increase in zinc oxide, decrease in Calcium D pantothenate (vitamin B5), and a decrease in maltodextrin. These are not changed in Table 1.

Batch 5 was same formulation as Batch 4 measured by weight for the 3 g final production serving size. Batch 5 mass produced for first production run.

The results are summarized in Table 2 below. Volunteers participated in the Study. Data for each volunteer includes batch number administered, the dosage amount of the formulation administered (mixed in 8-12 ounces water), the time at which the composition was administered following the onset of hangover symptoms, symptom improvement on a scale of 1 to 10 (10 being the greatest improvement), time to symptom improvement following administration, the number of administrations in a 24 hour period, and specific volunteer comments.

TABLE 2

| Batch | Dosage (mg) | Time Taken After Symptoms (min) | Symptom Relief (1 to 10)* | Time to Symptom Relief (min) | Doses in 24 Hours | Subject Comments |
| --- | --- | --- | --- | --- | --- | --- |
| 1 | 4.5 | 420 | 8 | 20 | 1 | no headache |
| 1 | 4.5 | 420 | 9 | 30 | 1 | like I didn't drink |
| 1 | 4.5 | 420 | 9 | 30 | 1 | no hangover |
| 1 | 4.5 | — | 9 | 15 | 1 | feel refreshed, clearer thinking |
| 1 | 4.5 | — | 9 | 15 | 1 | gave me more energy |
| 1 | 4.5 | 0 | 9 | 15 | 3 | took buzz away, couldn't get drunk |
| 1 | 4.5 | 0 | 10 | 10 | 3 | couldn't get really drunk |
| 1 | 4.5 | 0 | 9 | 15 | 2 | took buzz away, couldn't get drunk |
| 1 | 4.5 | 0 | 10 | 15 | 2 | couldn't get really drunk |
| 1 | 4.5 | 0 | 9 | 15 | 1 | kept buzz without hangover |
| 1 | 4.5 | 0 | 10 | 15 | 1 | took buzz away |
| 2 | 2 | 0 | 9 | 15 | 2 | kept buzz without hangover |
| 2 | 2 | 0 | 7 | 20 | 2 | no hangover |
| 2 | 2 | 0 | 8 | 30 | 1 | no hangover |
| 2 | 2 | 0 | 8 | 30 | 1 | no hangover |
| 2 | 2 | 0 | 7 | 20 | 1 | took feeling of too much alcohol away |
| 2 | 4.5 | 0 | 10 | 15 | 1 | cleared buzz |
| 2 | 4.5 | 0 | 10 | 15 | 1 | couldn't get drunk |
| 3 | 2.5 | 0 | 9 | 15 | 1 | no headache |
| 3 | 2.5 | 0 | 10 | 15 | 1 | no hangover |
| 4 | 2.5 | 30 | 10 | 20 | 1 | cleared headache |
| 4 | 2.5 | 30 | 10 | 20 | 1 | cleared headache |
| 4 | 3 | — | 10 | 30 | 1 | took without drinking and felt sharper, cleared out cobwebs |
| 4 | 3 | 300 | 10 | 20 | 1 | my headache was gone after about 20 minutes I felt fine as though I did not drink |

TABLE 2-continued

| Batch | Dosage (mg) | Time Taken After Symptoms (min) | Symptom Relief (1 to 10)* | Time to Symptom Relief (min) | Doses in 24 Hours | Subject Comments |
|---|---|---|---|---|---|---|
| 4 | 3 | 300 | 10 | 20 | 1 | Had to attend meeting the RVRS sobered me up so I was able to function - cleared my head and headache |
| 4 | 3 | 240 | 10 | 30 | 1 | took after drinking in a club for 3 hours. I felt much better within minutes I felt almost sober and able to clearly think again. It made me feel stable and no more headache |
| 4 | 3 | 300 | 10 | 20 | 1 | I had been drinking mixed drinks was very drunk. After drinking RVRS I felt new again, no longer drunk clear head no pain in my head |
| 4 | 3 | 300 | 10 | 20 | 1 | Drank all weekend one small bottle made me feel amazing no more hangover, headache, stomach ache, I was no longer tired |
| 4 | 3 | 300 | 10 | 20 | 1 | Needed to go to work this really made me sober undrunk and no more headache so I could go to work |
| 4 | 2.5 | 0 | 10 | 30 | 1 | started feeling less drunk |
| 4 | 2.5 | 10 | 10 | 30 | 1 | better right away |
| 4 | 2.5 | 10 | 8 | 30 | 1 | less drunk |
| 4 | 2.5 | 0 | 7 | 30 | 1 | sobered up a little |
| 4 | 2.5 | 0 | 8 | 45 | 1 | sobered up a little |
| 4 | 2.5 | 0 | 9 | 30 | 1 | less drunk |
| 4 | 2.5 | 0 | 9 | 30 | 1 | less buzzed |
| 4 | 2.5 | 0 | 8 | 30 | 1 | functioning better |
| 4 | 2.5 | 0 | 8 | 30 | 1 | less drunk |
| 4 | 2.5 | 0 | 8 | 30 | 1 | less drunk |
| 4 | 2.5 | 0 | 7 | 30 | 1 | less drunk |
| 4 | 2.5 | 0 | 7 | 15 | 1 | woke up |
| 4 | 2.5 | 30 | 9 | 20 | 1 | feeling better |
| 4 | 2.5 | 45 | 6 | 30 | 1 | less drunk |
| 4 | 2.5 | 10 | 8 | 20 | 1 | can drink more |
| 4 | 2.5 | 0 | 8 | 20 | 1 | less drunk |
| 4 | 2.5 | 0 | 8 | 15 | 1 | less drunk |
| 4 | 2.5 | 0 | 8 | 15 | 1 | less drunk |
| 4 | 2.5 | 5 | 8 | 20 | 1 | can drink more |
| 4 | 2.5 | 10 | 7 | 15 | 1 | less drunk |
| 4 | 2.5 | 0 | 7 | 15 | 1 | woke up |
| 4 | 2.5 | 0 | 9 | 10 | 1 | less drunk |
| 4 | 3 | 0 | 8 | 15 | 1 | less drunk |
| 4 | 3 | 0 | 9 | 10 | 1 | cleared buzz |
| 4 | 3 | 0 | 9 | 20 | 1 | cleared up fog |
| 4 | 3 | 0 | 9 | 15 | 1 | less buzzed |
| 4 | 3 | 0 | 8 | 10 | 1 | sobered up |
| 4 | 3 | 0 | 10 | 10 | 1 | can keep going |
| 4 | 3 | 0 | 10 | 15 | 1 | sobered up |
| 4 | 3 | 0 | 9 | 10 | 1 | no headache |
| 4 | 3 | 0 | 10 | 10 | 1 | less full |
| 4 | 3 | 0 | 10 | 15 | 1 | no stomach ache |
| 4 | 3 | 0 | 9 | 15 | 1 | less drunk |
| 4 | 3 | 0 | 9 | 20 | 1 | clearer |
| 4 | 3 | 0 | 10 | 15 | 1 | like I didn't drink |
| 4 | 3 | 0 | 10 | 10 | 1 | less buzzed |
| 4 | 3 | 0 | 10 | 10 | 1 | less drunk |
| 4 | 3 | 0 | 10 | 15 | 1 | can keep going |
| 4 | 3 | 0 | 9 | 15 | 1 | like I didn't drink too much |
| 4 | 3 | 420 | 10 | 20 | 1 | Was hung over/nauseous from night before. Took and almost immediately felt better. Can start drinking again. |
| 4 | 3 | 420 | 10 | 20 | 1 | Hung over from previous night. Headache and nausea gone after taking this. |
| 4 | 3 | 420 | 9 | 30 | 1 | Hung over from night before. This helped with headache and nausea going away. |
| 4 | 3 | 240 | 10 | 30 | 1 | cleared my headache and hangover feeling felt so much better |

TABLE 2-continued

| Batch | Dosage (mg) | Time Taken After Symptoms (min) | Symptom Relief (1 to 10)* | Time to Symptom Relief (min) | Doses in 24 Hours | Subject Comments |
|---|---|---|---|---|---|---|
| 4 | 3 | 300 | 10 | 20 | 1 | I was very hungover when i woke up drank one bottle felt immediate improvement was able to think and move again. my headache was gone |
| 4 | 2.5 | 30 | 10 | 20 | 1 | made me wake up without hangover |
| 4 | 3 | 300 | 10 | 20 | 1 | took after drinking at concert drinking for 6 hours prior to taking. Felt immediate relief, headache gone, stomach relief fuzzy brain gone within minutes |
| 4 | 3 | 300 | 10 | 20 | 1 | The one drink cleared up the my tiredness and headache from drinking |
| 4 | 3 | 240 | 10 | 20 | 1 | Used after I celebrated - instant sober no more drunkenness, clear head clear mind ready to go again |
| 4 | 3 | 20 | 10 | 20 | 1 | headache gone, sober |
| 4 | 3 | 300 | 10 | 20 | 1 | took after drinking before bed wok up feeling fresh and clear no headache |
| 4 | 3 | 240 | 10 | 30 | 1 | cleared my headache |
| 4 | 3 | 240 | 10 | 20 | 1 | helped relieve my headache, cleared my mind and sobered me up |
| 4 | 3 | 240 | 10 | 15 | 1 | no longer drunk |
| 4 | 3 | 240 | 10 | 20 | 1 | not dizzy |
| 4 | 3 | 240 | 10 | 25 | 1 | felt better almost immediately |
| 4 | 3 | 30 | 9 | 15 | 1 | helped with energy/headache |
| 4 | 3 | 60 | 10 | 12 | 1 | able to drink more |
| 4 | 3 | 60 | 10 | 10 | 1 | wasn't drunk anymore |
| 4 | 3 | 60 | 8 | 15 | 1 | was able to get out of bed |
| 4 | 3 | 120 | 9 | 15 | 1 | woke up normal |
| 4 | 3 | 120 | 9 | 15 | 1 | was able to go to work |
| 4 | 3 | 300 | 10 | 20 | 1 | cured my new years hang over within 20 minutes felt fresh and alive |
| 4 | 3 | 300 | 10 | 20 | 1 | after celebrating the new year I was able to clear my headache with just one dose |
| 4 | 3 | 240 | 10 | 20 | 1 | I was sick from drinking cured me instantly with one dose of RVRS I had a headache, stomach and was dizzy all gone |
| 4 | 3 | 720 | 9 | 60 | 1 | no headache |
| 4 | 3 | 720 | 9 | 60 | 1 | no headache |
| 4 | 3 | 30 | 8 | 45 | 1 | no hangover |
| 4 | 3 | 30 | 8 | 45 | 1 | improved nausea |
| 4 | 3 | 300 | 10 | 20 | 1 | RVRS cured my aching head i was able to sober up and feel normal |
| 4 | 3 | — | 10 | 30 | 2 | helped with upset stomach |
| 4 | 3 | — | 10 | 30 | 2 | helped with upset stomach |
| 4 | 3 | 60 | 7 | 30 | 1 | energy back |
| 4 | 3 | 60 | 8 | 15 | 1 | no hangover |
| 4 | 3 | 60 | 8 | 20 | 1 | helped stomach |
| 4 | 3 | 60 | 9 | 30 | 1 | no hangover |
| 4 | 3 | 60 | 7 | 20 | 1 | improved slowness |
| 4 | 3 | 60 | 9 | 20 | 1 | felt much better |
| 4 | 3 | 60 | 9 | 15 | 1 | no headache |
| 4 | 3 | 60 | 10 | 30 | 1 | no hangover |
| 4 | 3 | 60 | 7 | 30 | 1 | like I didn't drink |
| 4 | 3 | 60 | 10 | 30 | 1 | no hangover |
| 4 | 3 | 300 | 10 | 20 | 1 | took one glass before bed woke up in the morning feeling fine like I never drank |
| 4 | 3 | 60 | 10 | 15 | 1 | helped with hangover |
| 4 | 3 | 0 | 9 | 15 | 1 | woke up as if did not drink |
| 4 | 3 | 0 | 10 | 20 | 1 | didn't wake up with hangover |
| 4 | 3 | 60 | 10 | 10 | 1 | helped with spins |
| 4 | 3 | 60 | 10 | 10 | 1 | no hangover |

TABLE 2-continued

| Batch | Dosage (mg) | Time Taken After Symptoms (min) | Symptom Relief (1 to 10)* | Time to Symptom Relief (min) | Doses in 24 Hours | Subject Comments |
|---|---|---|---|---|---|---|
| 4 | 3 | 120 | 9 | 15 | 1 | felt way better |
| 4 | 3 | 120 | 9 | 15 | 1 | as if I didn't drink |
| 4 | 3 | 240 | 10 | 20 | 1 | was able to wake up next morning |
| 4 | 3 | 240 | 10 | 20 | 1 | got rid of hangover |
| 4 | 3 | 240 | 10 | 20 | 1 | cleared my head |

What is claimed is:

1. A composition for treating and/or preventing a hangover, the composition comprising:
   an amount of *Hovenia dulcis* fruit extract in a dosage range of about 10 mg to about 1000 mg per unit dose;
   an amount of prickly pear extract in a dosage range of about 50 mg to about 1000 mg per unit dose;
   an amount of L-glutathione in a dosage range of about 5 mg to about 100 mg per unit dose; and
   an amount of N-acetyl L-cysteine in a dosage range of about 50 mg to about 500 mg per unit dose;
   wherein the composition is formulated for oral delivery.

2. A composition for treating and/or preventing a hangover, the composition comprising:
   amounts of one or more minerals in a dosage range of about 1 mg to about 500 mg per unit dose;
   an amount of prickly pear extract in a dosage range of about 50 mg to about 1000 mg per unit dose;
   an amount of ginger root extract in a dosage range of about 50 mg to about 1000 mg per unit dose;
   an amount of L-glutathione in a dosage range of about 5 mg to about 100 mg per unit dose; and
   an amount of N-acetyl L-cysteine in a dosage range of about 50 mg to about 500 mg per unit dose;
   wherein the composition is formulated for oral delivery.

3. A composition for treating and/or preventing a hangover, the composition comprising:
   an amount of milk thistle in a dose range of about 100 mg to about 2000 mg per unit dose;
   amounts of one or more minerals in a dosage range of about 1 mg to about 500 mg per unit dose;
   amounts of one or more B vitamins in a dosage range of about 0.01 µg to about 100 mg per unit dose; and
   an amount of green tea leaf extract in a dosage range of about 10 mg to about 500 mg per unit dose;
   an amount of L-glutathione in a dosage range of about 5 mg to about 100 mg per unit dose; and
   an amount of N-acetyl L-cysteine in a dosage range of about 50 mg to about 500 mg per unit dose;
   wherein the composition is formulated for oral delivery.

4. The composition of any one of claims 1-3, further comprising:
   an amount of activated charcoal in a dosage range of about 1 mg to about 1000 mg per unit dose.

5. A method for treating and/or preventing a hangover in a subject in need thereof, the method comprising providing to the subject for oral administration the composition of claim 4.

6. A method of claim 5, wherein the composition is administered orally one, two, three or four doses per day.

* * * * *